(12) United States Patent
Olsbye et al.

(10) Patent No.: US 6,967,182 B1
(45) Date of Patent: Nov. 22, 2005

(54) CATALYSTS CONSISTING OF METALS ON HYDROTALCITE-BASED CARRIER MATERIALS, AND METHOD FOR THE PREPARATION THEREOF

(75) Inventors: Unni Olsbye, Oslo (NO); Duncan Akporiaye, Oslo (NO); Erling Rytter, Trondheim (NO); Morten Rønnekleiv, Trondheim (NO)

(73) Assignee: Den Norske Stats Oljeselskap, Stavanger (NO)

( * ) Notice: Subject to any disclaimer, the term of this patent is extended or adjusted under 35 U.S.C. 154(b) by 0 days.

(21) Appl. No.: 09/869,042

(22) PCT Filed: Dec. 22, 1999

(86) PCT No.: PCT/NO99/00403

§ 371 (c)(1),
(2), (4) Date: Oct. 3, 2001

(87) PCT Pub. No.: WO00/38832

PCT Pub. Date: Jul. 6, 2000

(30) Foreign Application Priority Data

Dec. 23, 1998 (NO) .................................. 986116

(51) Int. Cl.$^7$ ............................................. B01J 21/16
(52) U.S. Cl. .................................. 502/84; 502/80
(58) Field of Search .................... 502/80, 84; 585/660, 585/654

(56) References Cited

U.S. PATENT DOCUMENTS

| | | | |
|---|---|---|---|
| 4,866,019 A | * 9/1989 | van Broekhoven | 502/65 |
| 5,245,096 A | * 9/1993 | Derouane et al. | 585/419 |
| 5,276,233 A | * 1/1994 | Blom et al. | 585/419 |
| 5,518,704 A | 5/1996 | Kelkar et al. | |
| 6,313,063 B1 | * 11/2001 | Rytter et al. | 502/327 |

FOREIGN PATENT DOCUMENTS

| | | |
|---|---|---|
| EP | 0475357 | 3/1992 |
| EP | 0476489 | 3/1992 |
| WO | 9414700 | 7/1994 |
| WO | WO 94/29021 | * 12/1994 |
| WO | 9915459 | 4/1999 |

* cited by examiner

*Primary Examiner*—Christina Johnson
(74) *Attorney, Agent, or Firm*—Wenderoth, Lind & Ponack, L.L.P.

(57) ABSTRACT

The present invention relates to a catalyst comprising at least one metal loaded on a hydrotalcite-based carrier material which has the following formula in its uncalcined form: $M^{2+}{}_a M^{3+}{}_b (A^{n-})(OH)_{2a+3}b{-}n*xH_2O$, wherein $M^{2+}$ is at least one divalent metal; and $M^{3+}$ is at least one trivalent metal; A is an n-valent anion, n is 1 or 2 and a and b are positive numbers, a>b. When said at least one metal is selected from the group VIII of the periodical system of the elements a useful (de)hydrogenation catalyst is achieved.

2 Claims, 6 Drawing Sheets

Figure 1A:
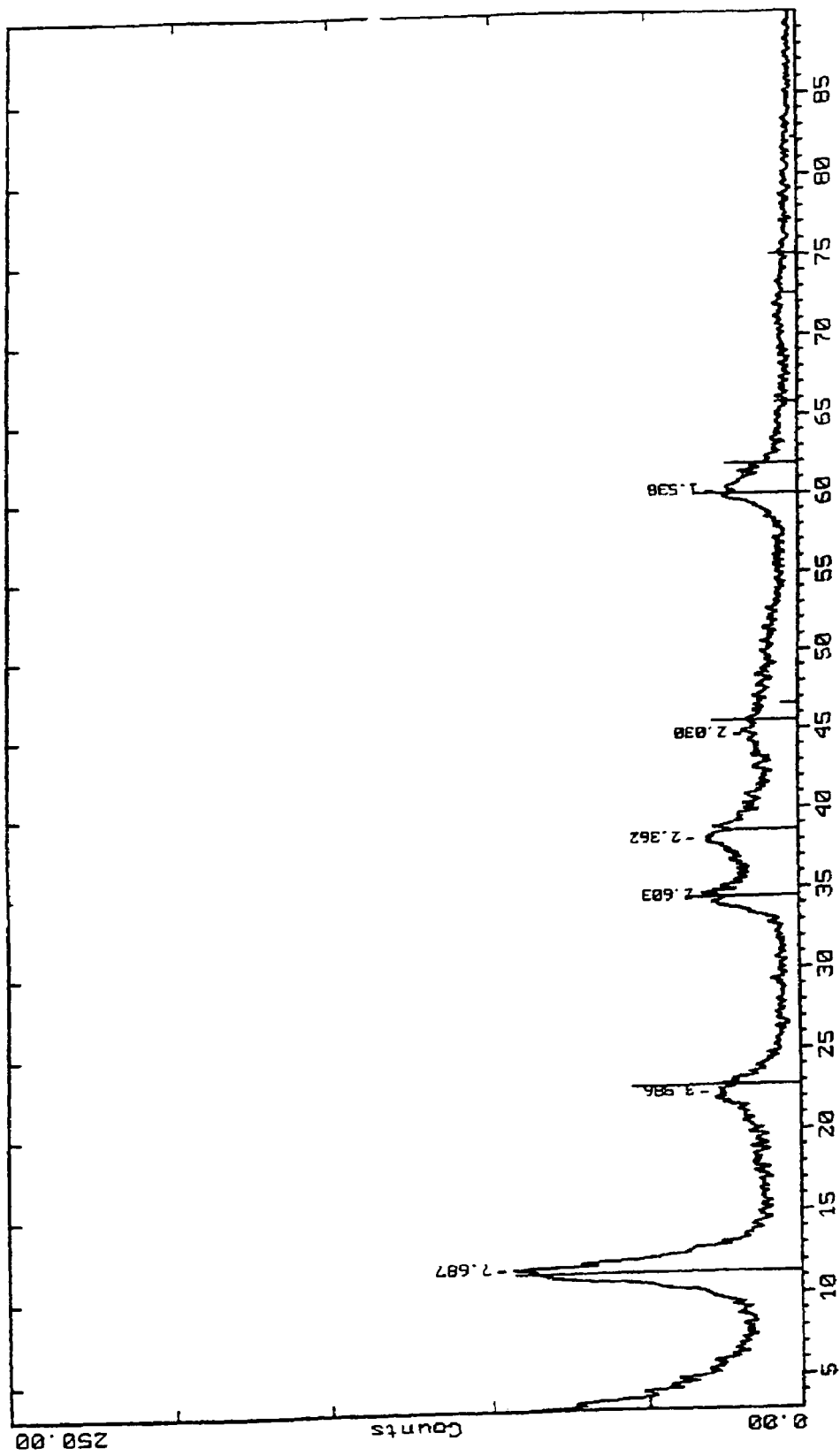

CATALYSTS CONSISTING OF METALS ON HYDROTALCITE-BASED CARRIER MATERIALS, AND METHOD FOR THE PREPARATION THEREOF

This application is a 371 application of PCT/NO99/00403 filed Dec. 22, 1999.

FIELD OF THE INVENTION

The present invention relates to catalysts. Particularly the invention relates to (de)hydrogenation catalysts. The invention further relates to the processes of preparing such catalysts. The invention also relates to the use of such catalysts in catalytic processes, particularly for the dehydrogenation of paraffins. Further the invention relates to processes of preparing alkenes by the use of such dehydrogenation catalysts, and to the hydrogenation of unsaturated hydrocarbons by the use of such catalysts.

BACKGROUND OF INVENTION

In a previous invention[1], it has been shown that catalysts with excellent activity and stability properties for the catalytic dehydrogenation of light paraffins may be obtained by deposition of a Group VIII metal, a Group IVA metal and, optionally, a Group IA metal, on a mixed oxide carrier material, Mg(Al)O. The mixed oxide carrier material is characterised by a high surface area (typically 100–300 m$^2$/g) and a high stability towards sintering. In a more recent invention[2], it was shown that improved stability of the carrier material is obtained by increasing the M$^{2+}$/M$^{3+}$ ratio (>2) and by increasing the calcination temperature (700–1200° C.).

Mixed M$^{2+}$ (M$^{3+}$)O materials may be obtained by calcination of a hydrotalcite-like material (HTC) of general formula:

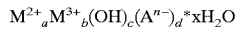

$$M^{2+}{}_a M^{3+}{}_b (OH)_c (A^{n-})_d \cdot xH_2O$$

at temperatures in the range 350–800° C.[3]. The transformation to the mixed oxide phase may be (partly) reversible, depending on the elements, which constitute the original HTC material, the preparation method, as well as the calcination conditions[3]. It has been reported that a M$^{2+}$ (M$^{3+}$)O material, that had been calcined at 500° C., regained it's hydrotalcite-like structure after contacting it with water[e.g.: 4,5]. It has further been reported that when hydrotalcite-like materials are used as ion-exchange materials for cleaning cooling water, such materials have a much higher ion uptake capacity when contacted with an aqueous solution after calcination to the oxide structure, than the corresponding uncalcined materials[4,5]. The explanation that was suggested is that ions present in the aqueous solution are taken up as constituent components in the structure as it is re-converted to the hydrotalcite-like form[4].

In the literature, numerous examples may be found relating to the use of hydrotalcite-like materials as catalysts or catalyst carriers[e.g.: 3]. Due to it's layered structure, hydrotalcite-like materials and the calcined analogs offer a variety of possibilities for insertion of an active metal, or of a promoter compound, as illustrated by the following examples:

The active metal may be introduced as one of the hydrotalcite cation components, followed by partial decomposition of the structure near the catalyst surface, by which the active metal component is released (e.g. Ni—Al—O compounds for use in steam reforming[6]).

The active metal may be impregnated on a hydrotalcite-based carrier (e.g. Pt on Mg—Al—O used for aromatisation of n-hexane[7]).

The active metal may be introduced as anions by anion exchange in the interlayer space (e.g. Mo- or V-containing HTC-based catalysts for the oxidative dehydrogenation of hydrocarbons[8]).

The impregnation methods that have been published to date, and which are relevant for the present invention, may be illustrated by the following examples:

In[9], a Ru/Mg(Al)O catalyst is prepared by dissolving RuCl$_3$ in water and >>throwing into the flask in one go>> a (Mg—Al—O type) hydrotalcite in the hydroxycarbonate or oxide form. The resulting material is centrifuged, vacuum-dried and, optionally, heat-treated at 500° C. in N$_2$. It is then reduced and used for the hydrogenation of aromatic hydrocarbons at 150° C. In[10], the invention is extended to involve other platinum group metals, preferably Pd.

In[11], Pt and/or Pd salt is dissolved in a solvent (preferably water), followed by spraying it onto a hydrotalcite support, or (preferably) soaking the hydrotalcite support in the solution. It is underlined that the pH of the solution must be at least about 5 or higher (preferably 6–8), in order to avoid damage of the hydrotalcite. After the metal deposition step, the product is heated to 200–400° C. in an inert or oxidising atmosphere, and reduced at about 50–450° C., before using it as a catalyst for CO oxidation in the temperature range (−60)–400° C.

In[7], a calcined hydrotalcite, Mg(Al)O, is impregnated with Pt(NH$_3$)$_4$Cl$_2$ in aqueous solution, dried, calcined in air at 380° C. and reduced in H$_2$ at 430° C. prior to using it as an n-hexane aromatisation catalyst at 480° C. A patent corresponding to the said publication covers (in claim 1) <<aromatisation catalysts comprising a Group VIII metal on a hydrotalcite-type support having in its uncalcined form a hydroxycarbonate structure>>[12].

In[13], Pt/Mg(Al)O catalysts were prepared by various methods and the final materials compared as n-hexane aromatisation catalysts. Prior to impregnation, the hydrotalcite was calcined at 600° C. for 12–15 hrs. XRD analysis showed diffuse peaks corresponding to MgO after calcination. Impregnation was performed by either incipient wetness impregnation of H$_2$PtCl$_6$ from an aqueous solution, leading to re-generation of the HTC structure, by vapour phase impregnation of Pt(acac)$_2$, or by liquid phase impregnation of Pt(acac)$_2$ dispersed in acetone. During impregnation of Pt(acac)$_2$ from vapour phase or from acetone, the MgO structure of the carrier material was maintained. After impregnation, the catalysts were calcined at 350° C./6 h and reduced in flowing H$_2$ at 400° C./2 h. During calcination, the MgO phase was partly regenerated for the catalyst impregnated from aqueous solution. H$_2$ chemisorption measurements showed that vapour impregnation gave twice as high metal dispersion (H/Pt=1.4) compared to liquid impregnation from aqueous or acetone solution (H/Pt=0.5). n-hexane aromatisation experiments showed that the catalyst prepared from an acidic metal precursor in aqueous solution led to a higher selectivity towards cracking than the other catalysts. This effect was explained by a higher acidity of the metal complex impregnated from aqueous phase. Impregnation of the catalysts with an alkali metal (K) led to improved benzene selectivity.

In our group's previous inventions, an organic solvent was used for metal deposition[1,2]. The choice of an organic solvent was based on two observations:

First, the materials were to be used at elevated temperatures, where the hydrotalcite is known to be transformed to a MgO structure. The high surface area of the calcined carrier material (typically 100–300 m²/g) compared to the hydrotalcite phase (typically <50 m²/g) was believed to give the best dispersion of the active components (compared to restoration of the hydrotalcite during aqueous impregnation).

Second, the Group IVA metal salt, which is preferably tin in the previous invention[1], was known to have a higher solubility in organic solvents than in water[14]. It is known in the art that tin-containing salts may be dissolved in water after the addition of an inorganic acid, or a mixture of an inorganic and an organic acid[15]. In the course of the present work, it was discovered that Group IVA metal salts may also be dissolved in water acidified with an organic acid alone. It was further discovered that both aqueous and organic solutions containing Pt and Sn turned red upon dissolution of $SnCl_2$, indicating the formation of a Pt-Sn complex.

Due to environmental concerns, organic solvents may not be the optimal choice for catalyst preparation at a commercial plant scale. Based on such concerns, the original aim of the present work was to develop a metal deposition method based on aqueous metal salt solutions. Surprisingly, it was found that an aqueous suspension of the $M^{2+}$ ($M^{3+}$)O carrier material, leading to the reformation of the hydrotalcite-like phase during metal addition, leads to catalysts with improved activity and stability properties compared to those obtained by metal addition to the calcined $M^{2+}$ ($M^{3+}$)O phase.

Under industrial conditions, catalyst pellets of a certain size must be used in order to reduce the pressure drop through the catalyst bed, especially in fixed-bed reactors. In order to increase the mechanical strength of the catalyst pellets, binder materials are often added before pelletisation. Alumina is often used for this purpose.[17]

Catalytic dehydrogenation of hydrocarbons is a well-known and commercially important process (16). The reactions follow the general reaction equation:

$$C_nH_{2n+2} = H\ C_nH_{2n} + H_2 \qquad (i)$$

Dehydrogenation reactions are strongly endothermic, and the conversion is limited by thermodynamic equilibrium. As an example, the equilibrium conversion for the catalytic dehydrogenation of propane is approx. 62% under the conditions used in the present work. The Gibbs energy of reaction (i) becomes more favorable with increasing temperatures, leading to higher equilibrium conversions. The equilibrium conversion at a given temperature further decreases with increasing pressure, and increases with an increasing chain-length (n). The major byproducts from dehydrogenation reactions are lighter hydrocarbons resulting from cracking reactions, as well as coke. Hydrogenolysis of the reactant, as well as hydrogenation of unsaturated products, may also occur. Coke formation leads to catalyst deactivation through encapsulation of the active site, and coke must be gasified in regeneration cycles. In some cases, steam is added to the process to prevent coke formation. In those cases, $CO_x$ may be formed from steam reforming of the hydrocarbons.

SUMMARY OF INVENTION

This invention relates to a method for preparing catalysts consisting of metals (in any oxidation state) on a $M^{2+}$ ($M^{3+}$)O support, where $M^{2+}$ is one or a combination of several divalent cation(s), such as Mg, Ni, Co, Cr, and $M^{3+}$ is one or a combination of several trivalent cation(s), such as Al, Ga, Cr, Co. The said catalyst is obtained by addition of metal(s) to the support while the latter is (at least partly) in, or transformed to, a hydrotalcite phase, followed by washing and calcination to obtain the final catalyst.

Prior to metal deposition, the support material may have been subject to preparation; preparation and drying; preparation, drying and calcination; preparation, drying, calcination and suspension; preparation and anion-exchange, or any other combination of the said methods, as well as any other method known in the art for obtaining a hydrotalcite-like phase.

The metal(s) to be added to the carrier material may exist as organic or inorganic metal salts or complexes, or as a mixture of such salts and complexes. Prior to addition, the metals may or may not be dissolved in an organic solvent, such as ethanol, acetone, or in an aqueous solution. The aqueous solution may have a neutral pH, or it may have been acidified by using an inorganic acid, such as e.g. HCl, $HNO_3$, or it may have been acidified by using an organic acid, such as e.g. acetic acid, citric acid, oxalic acid; or by using a mixture of organic and inorganic acids.

The solvent may also consist of both an organic solvent and water with or without an organic acid and/or an inorganic acid.

The metal addition may proceed through wet impregnation, incipient wetness impregnation, spraying, vapour deposition or any other method known in the art. The metal addition may take place while the carrier material is in a suspension, or on a dry or wetted carrier material in a fixed bed, a fixed moving bed or a fluidized bed state. Addition of several metals may proceed simultaneously or in a sequential order. When performed simultaneously, the several metals may be present as individual ions, or in mixed complex ions. The wet impregnation contact time may range from 0.01 to 30 hours, preferably about 0.05 to 5 hours.

After the metal addition step, the resulting material is optionally filtered and/or washed and/or dried, and finally heated in an inert or oxidizing atmosphere in order to obtain a catalyst with a high surface area, high sintering resistance and high and stable metal dispersion. Before using it as a catalyst, the material may optionally be treated in a reducing atmosphere under conditions which lead to an optimal oxidation state of the active metal(s).

Thus the present invention particularly relates to a catalyst comprising at least one metal loaded on a hydrotalcite-based carrier material which has the following formula in it's uncalcined form $$M^{2+}{}_aM^{3+}{}_b(A^{n-})_c(OH)_{2a+3b-nc}*xH_2O,$$

wherein $M^{2+}$ is at least one divalent metal; and $M^{3+}$ is at least one trivalent metal;

A is an n-valent anion n is 1 or 2, c is 1 or 2, and a and b are positive numbers, a>b;

the catalyst being prepared by;

a) addition of at least one metal salt or complex to the carrier material, of which the carrier material is (at least partly) in, or transformed to, the hydrotalcite phase during the metal addition step;

b) followed by washing, and c) calcination.

Particularly the invention relates to a (de)hydrogenation catalyst comprising at least one metal selected from each of the group VIII (group IVA and group IA) of the periodical table of elements loaded on a hydrotalcite-based carrier material which has the following formula in it's uncalcined form $$M^{2+}{}_a M^{3+}{}_b (A^{n-})_c (OH)_{2a+3b-nc} * xH_2O,$$

wherein $M^{2+}$ is at least one divalent metal; and $M^{3+}$ is at least one trivalent metal;
A is an n-valent anion
n is 1 or 2,
c is 1 or 2
and a and b are positive numbers, a>b;

the catalyst being prepared by:
a) addition of at least one metal salt or complex to the carrier material, of which the carrier material is (at least partly) in, or transformed to, the hydrotalcite phase during the metal addition step; followed by
b) washing, and
c) calcination.

In a preferred embodiment $M^{2+}$ is at least one divalent metal selected from the group consisting of Mg, Ni, Zn, Fe, Co, Cu, Cr, Mn, Ru, Rh, Pd, Os, Ir, Pt; and $M^{3+}$ is at least one trivalent metal selected from the group consisting of Al, Ga, Ni, Co, Fe, Cr, Mn, V, Ti;
A is OH and/or $CO_3$; $CH_3COO$; or other inorganic or organic acid residues n is 1 or 2.
Preferably $M^{2+}$ is Mg.
Further $M^{3-}$ is preferably Al.
Optionally $M^{3+}$ is further Ga.

According to one option the at least one metal salt or complex has been added in an aqueous solution.

In that case the at least one metal salt or complex may have been added in an aqueous neutral solution.

Further the at least one metal salt or complex may have been added in an acid aqueous solution.

In that case it is preferred that the pH of the acid aqueous solution is lower than 5, and preferably lower than 4.

According to a preferred embodiment thereof the at least one metal salt or complex has been added in an aqueous inorganic acid solution.

A preferred aqueous solution is an aqueous HCl solution.

The acid aqueous solution may also be a solution of an organic acid such as acetic acid.

Another option is that the at least one metal salt or complex has been added in an organic solution.

The addition of the at least one metal salt or complex has then according to a preferred embodiment been performed in an ethanol solution.

According to another option of the invention the at least one metal salt or complex has been added by wet impregnation.

The contact time between the metal containing solution and the carrier material may be between 0.01–30 hours, preferably between 0.05–5 hours.

According to a further option of the invention the at least one metal salt or complex may have been added by incipient impregnation.

The at least one metal salt or complex may also have been added by spraying.

At last the at least one metal salt or complex may further have been added by vapor deposition.

The hydrotalcite based carrier has preferably been prepared by mixing $Mg(NO_3)_2.6H_2O$ and $Al(NO_3)_3.9H_2O$ dissolved in water with a basic aqueous solution comprising OH and $CO_3$ anions.

Further the hydrotalcite based carrier may have been subject to drying.

In addition the hydrotalcite based carrier may have been subject to calcination.

Also the hydrotalcite based carrier may have been subject to the above mentioned preparation, drying and calcination followed by suspension.

The hydrotalcite based carrier may optionally have been subject to an anion exchange.

At last the hydrotalcite based carrier may have been subject to a combination of any of the treatments mentioned above.

The calcination temperature of the hydrotalcite based carrier is preferably in the range of about 700 to 1200° C., particularly about 700–800° C.

The final catalyst calcination takes preferably place at a temperature of about 400 to 1200° C., particularly about 560–800° C.

The catalyst may be admixed a binder.

In the case of the (de)hydrogenation catalyst the hydrotalcite based carrier has been impregnated by at least one metal selected from the group VIII of the periodical table of the elements.

Further in a preferred embodiment the hydrotalcite based carrier has been impregnated by at least one metal selected from the group IVA of the periodical table of the elements.

Particularly the hydrotalcite based carrier has been impregnated by at least one metal selected from the group VIII, at least one metal selected from the group IVA, and optionally at least one metal selected from the group IA of the periodical table of the elements.

Particularly the hydrotalcite based carrier has been impregnated by at least one salt or complex of Pt as the group VIII of the periodical table of the elements metal.

Suitably the hydrotalcite based carrier has been impregnated by at least one salt or complex of Sn from the group IVA of the periodical table of the elements.

In a particularly preferred embodiment of the invention the hydrotalcite based carrier has been impregnated by at least one salt or complex of Pt as the group VIII and by at least one salt or complex of Sn as the group IVA of the periodical table of the elements metal.

A preferred combination is the one wherein the hydrotalcite based carrier has been impregnated by a salt or complex of Pt and by a salt or complex of Sn.

The preferred salt of Pt is $H_2PtCl_6.6H_2O$.

The preferred the salt of Sn is $SnCl_2.2H_2O$.

Accordingly a catalyst as defined above is useful in a catalytic process.

When the catalytic metal is Pt the catalyst is particularly useful in dehydrogenation reactions, particularly in the dehydrogenation of alkanes.

Of particular interest is in the dehydrogenation of $C_{2-4}$ alkanes, such as the dehydrogenation of propane.

Use of the catalyst of the invention for the hydrogenation of unsaturated hydrocarbons is also subject matter of the present invention.

DETAILED DESCRIPTION OF INVENTION

The invention is illustrated by the following examples.

General:

Powder X-ray diffraction measurements were performed using a Siemens D-5000 diffractometer with Cu—$K_\alpha$ radiation. The specific surface area was measured using nitrogen by the BET method. XRD and BET analysis results are shown in Table 1 and in FIGS. 1–3.

Figure 1B:
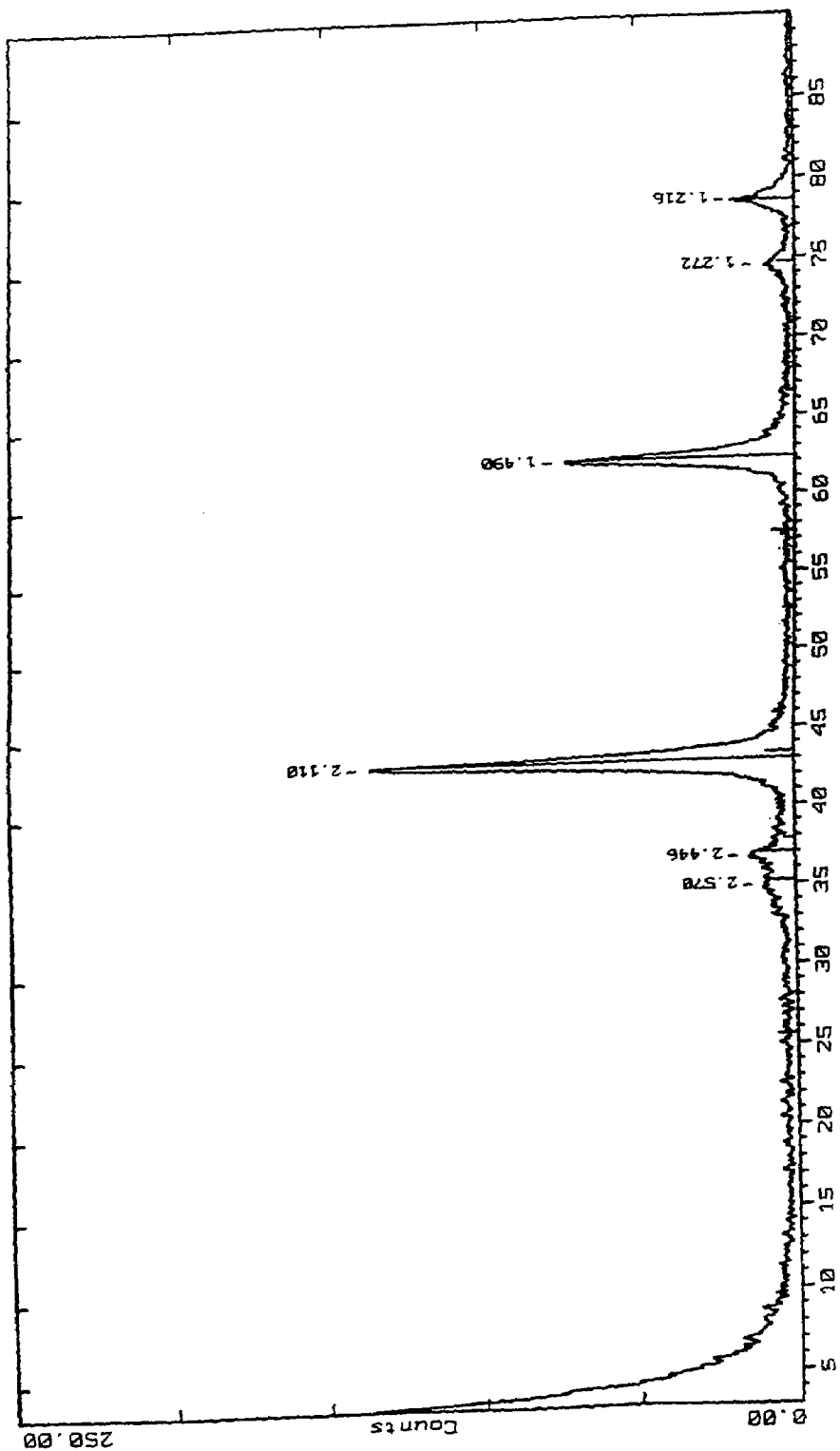

FIG. 1: X-ray diffractograms of a sample prepared according to Example 2; a) after drying, and b) after calcination.

Figure 2A:
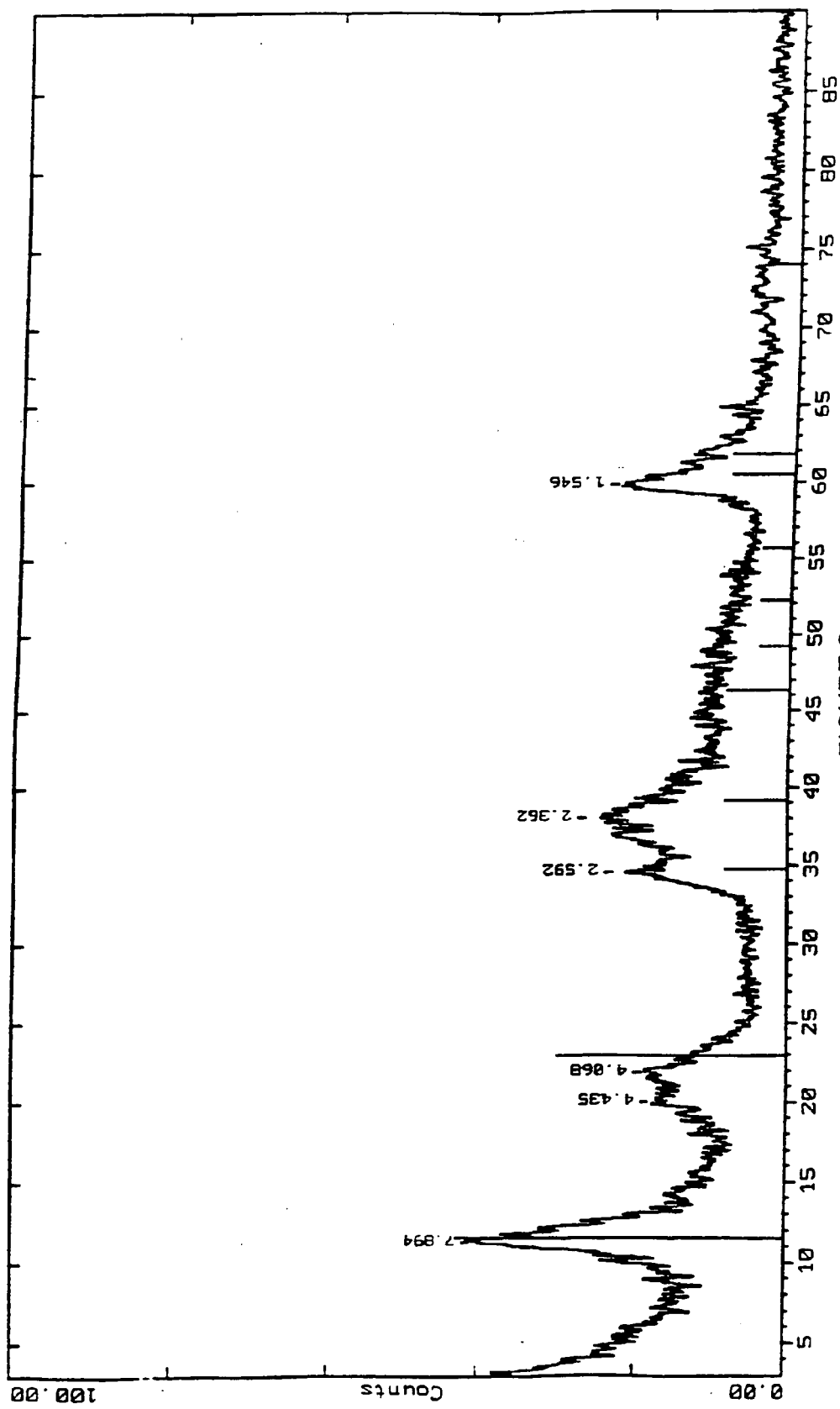
Figure 2B:
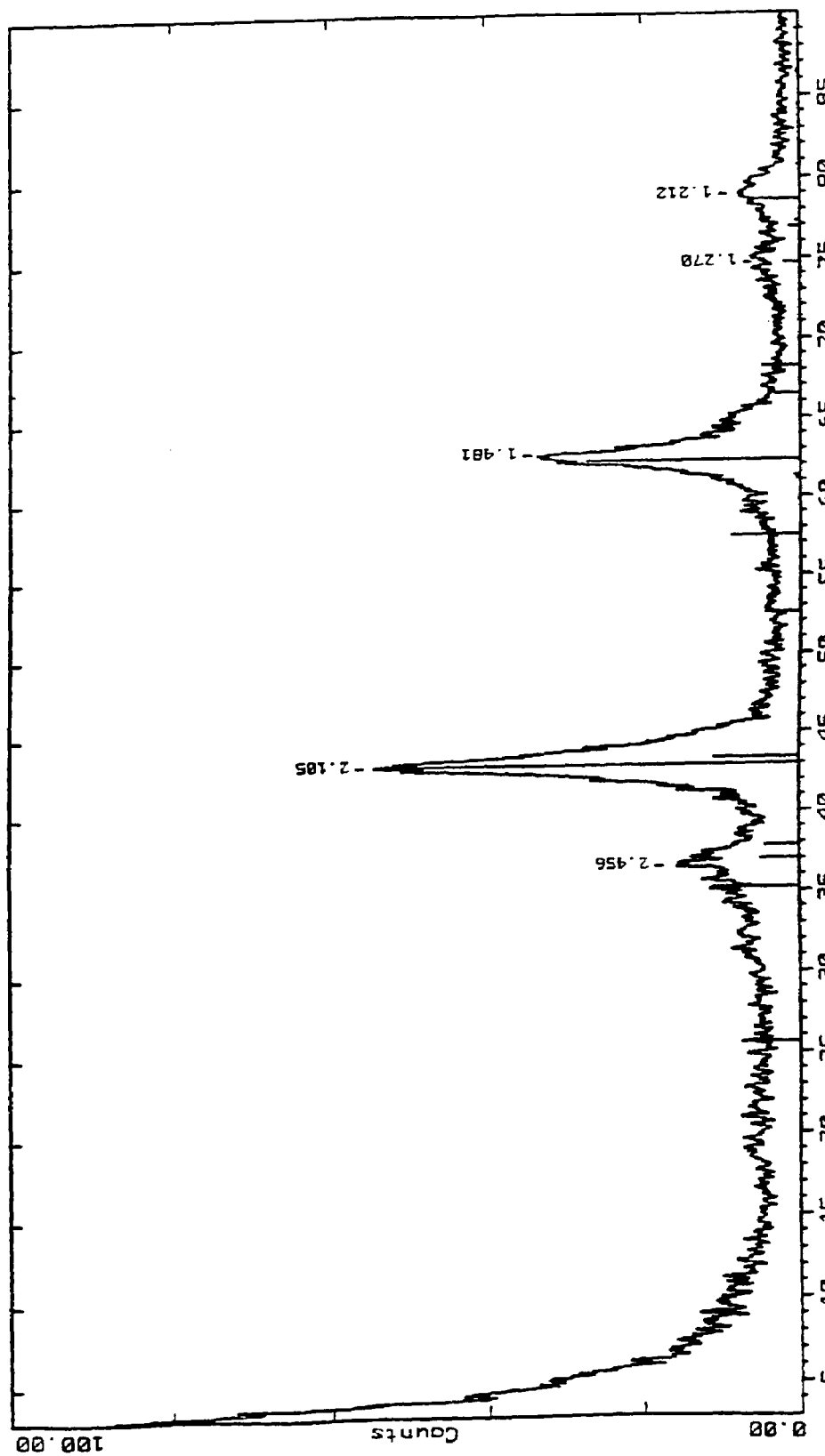

FIG. 2: X-ray diffractograms of a sample prepared according to Example 7; a) after impregnation, and b) after impregnation and calcination.

FIG. 3: X-ray diffractogram of a sample prepared according to Example 11; a) after impregnation, and b) after impregnation and calcination.

Calcination was performed under flowing air (100 Nml/min). The sample was heated with a heating rate of 3° C./min to the final calcination temperature. The duration of the calcination (at the final calcination temperature) was 15 hours for carrier materials, and 5 hours for catalysts. After completing the calcination, the sample was cooled with a cooling rate of appx. 2° C./min. Before testing, the catalyst powder was pressed to tablets (5 tons pressure, tablet diameter 24 mm), crushed and sieved to a particle diameter of 0.7–1.0 mm.

Catalytic testing in dehydrogenation reactions was performed in a fixed bed titanium reactor. The inner diameter of the reactor was 9 mm. A titanium tube of outer diameter 3 mm was located in the centre of the reactor. The reactor temperature was controlled by a thermocouple placed in the 3 mm tube inside the reactor. The catalyst pellets (appx. 3 g) were placed on a titanium sinter in the reactor. The total pressure in the reactor was 1.1 bar.

Product analysis was performed using an on-line Gas Chromatograph.

During propane dehydrogenation (PDH), the reaction temperature was 600° C. The GHSV was 1000 h$^{-1}$ based on propane, and the reaction gas contained 4.5% hydrogen, 32% propane and remainder steam, on a mole basis. The duration of each test cycle was 24 hours, including regeneration.

Prior to testing, the catalyst was activated in situ through an ROR (reduction-oxidation-reduction) treatment at 600° C. The ROR treatment is described in detail in[1].

Catalyst regeneration was performed by oxidative treatment using air diluted with nitrogen. The oxygen content was initially 2%, and was increased in a stepwise manner to a final level of 21% (pure air). After regeneration, the catalyst was reduced in flowing hydrogen. Both the regeneration and reduction steps were carried out at 600° C.

In the catalytic tests, the selectivity towards propene was generally 97–98%, on mole carbon basis. Conversion data from the tests are shown in Table 2.

Dehydrogenation of other feeds were performed according to the procedure described above, but at different temperatures and pressures:

Ethane dehydrogenation was performed at 600–700° C. with a feed ratio: Ethane:$H_2$:$H_2O$= 16.5:4.5:79 on a mole basis, and GHSV=500 h$^{-1}$ based on ethane. Iso-Butane dehydrogenation was performed at 570–600° C. with a feed ratio: Isobutane:$H_2$:$H_2O$=32 4.5:63.5 on a mole basis, and GHSV=1000 h$^{-1}$ based on isobutane. Propene hydrogenation was performed at 550° C. and 2 bar pressure, with a feed molar ratio: $C_3H_6$:$H_2$:$H_2O$=23:27:50. The GHSV was 1000 h$^{-1}$ based on propene.

EXAMPLE 1

Preparation of HTC Carrier Material a) Nitrate salts of magnesium ($Mg(NO_3)_2$*$6H_2O$, 116.35 g) and aluminium ($Al(NO_3)_3$*$9H_2O$, 17.01 g) were dissolved in distilled water (500 ml). A second solution was prepared from $(NH_4)_2CO_3$ (2.18 g) and $NH_3$ (25%, 21 ml) in distilled water (500 ml). The two solutions were slowly added (dropwise addition with 40 minutes duration) to a common reservoir under continuous stirring. The pH of the solution was kept constant at appx. 8, and the temperature was appx. 60° C. The final adduct was filtered, washed with distilled water to neutrality, and dried overnight (100° C.). The X-ray diffractogram showed a major hydrotalcite phase.

b) A part of the product was subject to calcination at 700° C. The transformation of the hydrotalcite phase into a Mg(Al)O structure was shown by XRD.

Chemical analysis of the resulting carrier material showed that it had a molar ratio: Mg/Al= 3.

EXAMPLE 2

Preparation of HTC Carrier Material a) Nitrate salts of magnesium ($Mg(NO_3)_2$*$6H_2O$, 233.24 g) and aluminium ($Al(NO_3)_3$*$9H_2O$, 34.02 g) were dissolved in distilled water (1000 ml). A second solution was prepared from $Na_2CO_3$ (4.80 g) and NaOH (45.31 g) in distilled water (1000 ml). The two solutions were slowly added (dropwise addition with 55 minutes duration) to a common reservoir under continuous stirring. The pH of the solution was kept constant at appx. 10, and the temperature was appx. 60° C. The final adduct was filtered, washed with distilled water to neutrality, and dried overnight (100° C.). The X-ray diffractogram showed a major hydrotalcite phase.

b) A part of the product was subject to calcination at 800° C. The transformation of the hydrotalcite phase into a Mg(Al)O structure was shown by XRD.

Chemical analysis of the resulting carrier material obtained during repeated preparations, showed that it had a molar ratio in the range Mg/Al=5.0±0.6. The carrier material used for metal addition had a Mg/Al ratio of 4.8.

XRD patterns of the dried and calcined materials are shown in FIG. 1.

EXAMPLE 3

Impregnation of a Calcined HTC Carrier Material from an Ethanol Solution a) A Mg—Al—O carrier material (61.95 g) prepared according to Example 1b was co-impregnated with $H_2PtCl_6$*$6H_2O$ (0.4930 g) and $SnCl_2$*$2H_2O$ (1.4133 g) in ethanol solution (500 ml). The solution was stirred with the carrier material for 2 hours, and the solvent evaporated under reduced pressure. The solid material was then dried (100° C.). Part of the material was calcined at 560° C. and tested under PDH conditions.

b) A Mg—Al—O carrier material (51.86 g) prepared according to Example 2b was co-impregnated with $H_2PtCl_6$*$6H_2O$ (0.3889 g) and $SnCl_2$*$2H_2O$ (1.1828 g) in ethanol solution (400 ml). The solution was stirred with the carrier material for 2 hours, and the solvent evaporated under reduced pressure. The solid material was then dried (100° C.). Part of the material was calcined at 560° C. and tested under PDH conditions.

EXAMPLE 4

Impregnation of a Calcined HTC Carrier Material from an Aqueous Solution Acidified by HCl, without Washing Tin chloride ($SnCl_2 \cdot 2H_2O$, 0.3181 g) was dissolved in HCl (2M, 51 ml). Hexachloroplatinum ($H_2PtCl_6 \cdot 6H_2O$, 0.1045 g) was dissolved in distilled water (91 ml). The two solution were mixed. A Mg—Al—O carrier material (13.9 g) prepared according to Example 1b was stirred with the salt solution for 30 minutes. The solution was then filtered, and the solid material dried (100° C.). The material was calcined at 560° C. and tested under PDH conditions.

EXAMPLE 5

Impregnation of a Calcined HTC Carrier Material from an Aqueous Solution Acidified by HCl Tin chloride ($SnCl_2 \cdot 2H_2O$, 0.3398 g) was dissolved in HCl (1M, 109 ml). Hexachloroplatinum ($H_2PtCl_6 \cdot 6H_2O$, 0.1116 g) was dissolved in distilled water (40 ml). The two solutions were mixed. A Mg—Al—O carrier material (14.88 g) prepared according to Example 1b was stirred with the salt solution for 30 minutes. The solution was then filtered, and washed 3 times with water (appx. 750 ml). The solid material was dried (100° C.). Part of the material was calcined (560° C.) and tested under PDH conditions.

EXAMPLE 6

Impregnation of a Calcined HTC Carrier Material from an Aqueous Solution Acidified by HCl Tin chloride ($SnCl_2 \cdot 2H_2O$, 0.2429 g) was dissolved in HCl (37%, 6.5 ml). Hexachloroplatinum ($H_2PtCl_6 \cdot 6H_2O$, 0.0793 g) was dissolved in distilled water. The two solutions were mixed and distilled water added to a total volume of 100 ml. The solution was mixed with a calcined Mg(Al)O material, prepared according to Example 2b (10.6 g). The suspension was stirred for 1 hour, filtered, washed and dried overnight (100° C.). The product was then calcined (560° C.) and tested under PDH conditions.

EXAMPLE 7

Impregnation of a Calcined HTC Carrier Material in Suspension, from an Aqueous Solution Acidified by HCl (Rapid Addition)

Tin chloride ($SnCl_2 \cdot 2H_2O$, 0.2482 g) was dissolved in HCl (2M, 32 ml). Hexachloroplatinum ($H_2PtCl_6 \cdot 6H_2O$, 0.082 g) was dissolved in distilled water (5 ml). The two solutions were mixed. Mg(Al)O (10.9 g), prepared according to Example 2b, was slurried in distilled water (60 ml). The suspension was stirred for some minutes, before the salt solution was rapidly added. The final suspension was stirred for 1 hour, filtered, washed and dried overnight (100° C.). The product was then calcined (560° C.) and tested under PDH conditions. XRD patterns of the dried and calcined materials are shown in FIG. 2.

EXAMPLE 8

Impregnation of a Calcined HTC Carrier Material in Suspension, from an Aqueous Solution Acidified by HCl (Dropwise Addition)

Tin chloride ($SnCl_2 \cdot 2H_2O$, 0.2094 g) was dissolved in HCl (37%, 5.6 ml). Hexachloroplatinum ($H_2PtCl_6 \cdot 6H_2O$, 0.0691 g) was dissolved in distilled water (10 ml). The two solution were mixed, and distilled water added to a total volume of 35 ml. Mg(Al)O (9.18 g), prepared according to Example 2b, was added to distilled water (85 ml). The suspension was stirred for some minutes, before the salt solution was added in a dropwise manner (10 min). The final suspension was stirred for 1 hour, filtered, washed and dried (100° C.). The product was then calcined (560° C.) and tested under PDH conditions. In the main test (Ex. 8a), the ordinary pretreatment procedure was used, while in a second test (Ex. 8b), a slightly modified pretreatment procedure was used.

EXAMPLE 9

Impregnation of a Calcined HTC Carrier Material in Suspension, from an Aqueous Solution Acidified by HCl, with Prolonged Contact Time Tin chloride ($SnCl_2 \cdot 2H_2O$, 0.2349 g) was dissolved in HCl (37%, 6 ml). Hexachloroplatinum ($H_2PtCl_6 \cdot 6H_2O$, 0.0774 g) was dissolved in distilled water (5 ml). The two solution were mixed, and distilled water added to a total volume of 45 ml. Mg(Al)O (10.3 g), prepared according to Example 2b, was added to distilled water (55 ml). The suspension was stirred for some minutes, before the salt solution was added in a dropwise manner (4-5 min). The final suspension was stirred for 3 hours, filtered, washed and dried overnight (100° C.). The product was then calcined (560° C.) and tested under PDH conditions.

EXAMPLE 10

Impregnation of a Calcined HTC Carrier Material in Suspension, from an Aqueous Solution Acidified by HCl, without Washing Tin chloride ($SnCl_2 \cdot 2H_2O$, 0.2015 g) was dissolved in HCl (37%, 5.5 ml). Hexachloroplatinum ($H_2PtCl_6 \cdot 6H_2O$, 0.0670 g) was dissolved in distilled water (10 ml). The two solution were mixed, and distilled water added to a total volume of 40 ml. Mg(Al)O (8.83 g), prepared according to Example 2b, was added to distilled water (45 ml). The suspension was stirred for some minutes, before the salt solution was added in a dropwise manner (10 min). The final suspension was stirred for 1 hour, filtered and dried overnight (100° C.). The product was then calcined (560° C.) and tested under PDH conditions.

EXAMPLE 11

Figure 3A:
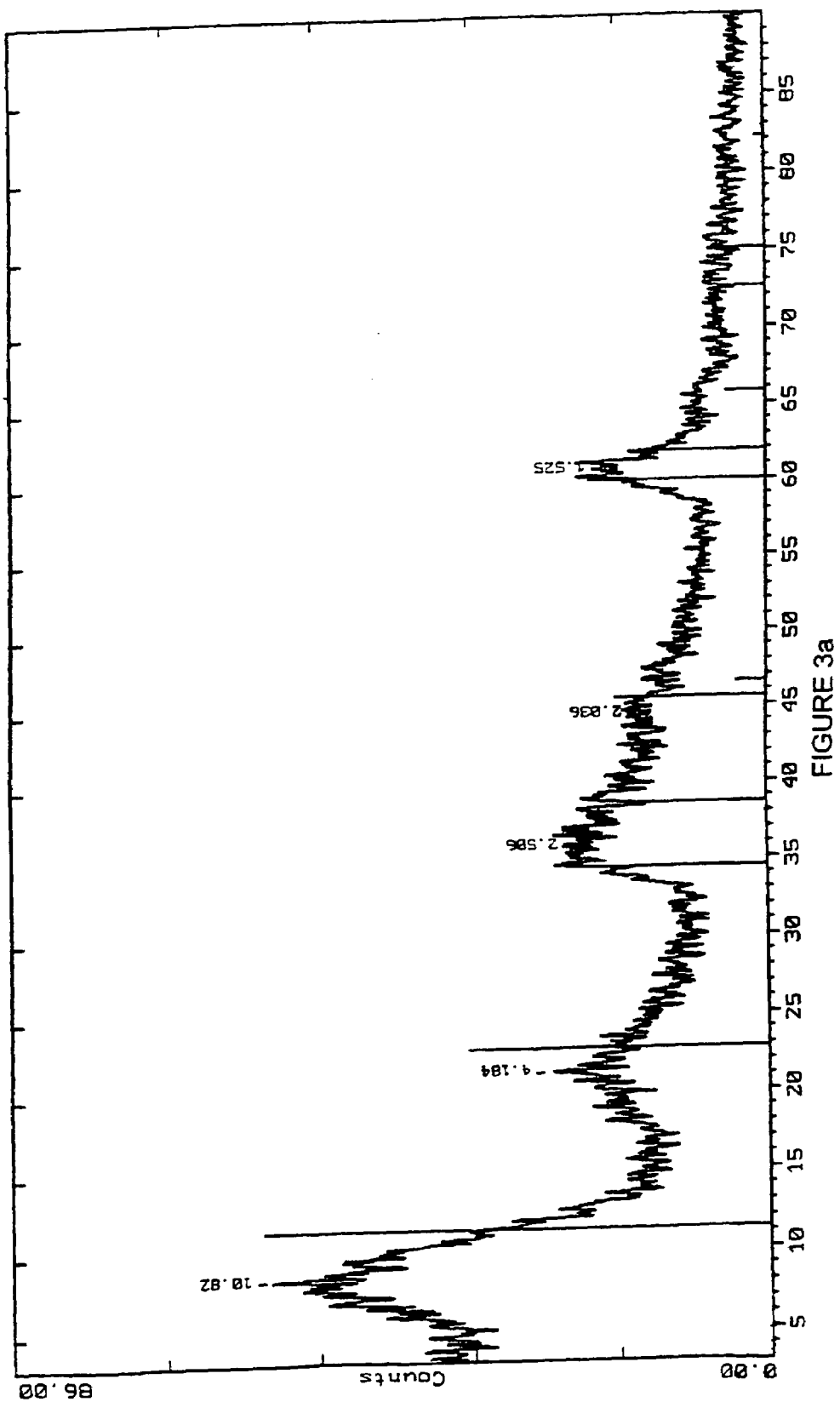
Figure 3B:
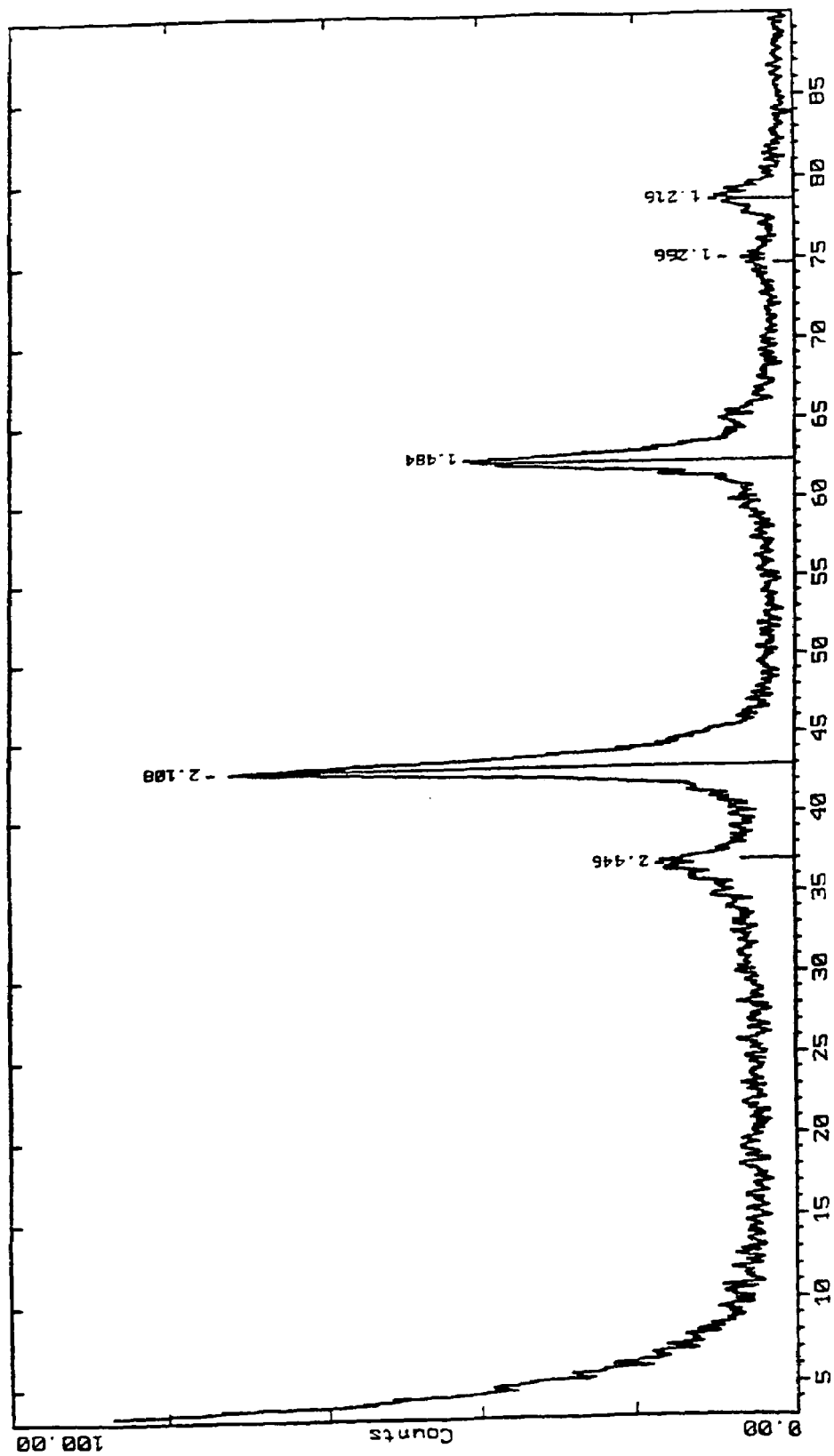

Impregnation of a Calcined HTC Carrier Material in Suspension, from an Aqueous Solution Acidified by Acetic Acid Tin chloride ($SnCl_2 \cdot 2H_2O$, 0.2355 g) and hexachloroplatinum ($H_2PtCl_6 \cdot 6H_2O$, 0.076 g) were dissolved in acetic acid (10 ml). Distilled water was added to a total volume of 50 ml. Mg(Al)O (10.2 g), prepared according to Example 2b, was added to distilled water (60 ml). The suspension was stirred for some minutes, before the salt solution was added in a dropwise manner (4–5 min). The final suspension was stirred for 0.5 hours, filtered and dried overnight (100° C.). XRD of the dried product showed the appearance of a poorly crystalline hydrotalcite. The d(001) value had been shifted to 10.82, indicating that the anion interlayer contains acetate anions, (FIG. 3a). The product was then calcined at 560° C. yielding the MgO phase (FIG. 3b).

EXAMPLE 12

Impregnation of an Uncalcined HTC Carrier Material in Suspension, from an Aqueous Solution Acidified by HCl a) Tin chloride ($SnCl_2*2H_2O$, 0.2046 g) was dissolved in HCl (37%, 6.0 ml). Hexachloroplatinum ($H_2PtCl_6*6H_2O$, 0.0677 g) was dissolved in distilled water (10 ml). The two solution were mixed, and distilled water added to a total volume of 40 ml. Mg—Al HTC (14.7 g), prepared according to Example 2a, was added to distilled water (50 ml). The suspension was stirred for some minutes, before the salt solution was added in a dropwise manner (10 min). The final suspension was stirred for 1 hour, filtered, washed and dried overnight (100° C.). Part of the product was then calcined (560° C.) and tested under PDH conditions.

b) Part of the dried product was calcined at 800° C. and tested under PDH conditions.

EXAMPLE 13

Impregnation of an Uncalcined HTC Carrier Material from an EtOH Solution

Tin chloride ($SnC_2*2H_2O$, 0.1779 g) and hexachloroplatinum ($H_2PtCl_6*6H_2O$, 0.0586 g) were dissolved in ethanol (75 ml). The solution were added to a Mg—Al HTC (12.78 g) carrier, prepared according to Example 2a. The suspension was stirred for 2 hours, and the solvent evaporated under reduced pressure. The solid material was dried (100° C.), calcined (560° C.) and tested under PDH conditions.

EXAMPLE 14

Preparation of Hydrotalcite Material Containing Mg and Ga, with Subsequent Impregnation Nitrate salts of magnesium ($Mg(NO_3)_2*6H_2O$, 73.80 g) and gallium ($Ga(NO_3)_3*9H_2O$, 13.411 g) were dissolved in distilled water (750 ml). A second solution was prepared from $K_2CO_3$ (3.355 g) and KOH (22.57 g) in distilled water (750 ml). Distilled water (300 ml) was added to a reservoir and heated to 50° C. The two solutions were added to this reservoir in a dropwise manner (total duration 40 minutes) under continuous stirring. The pH of the solution was kept constant at appx. 10, and the temperature was appx. 45° C. The final adduct was filtered, washed with distilled water and dried overnight (100° C.). The X-ray diffractogram showed a hydrotalcite phase.

Part of the material was calcined (800° C.) and impregnated with Pt and Sn according to Example 8.

EXAMPLE 15

Impregnation of a Wet, Uncalcined HTC Carrier Material in Suspension, from an Aqueous Solution Acidified by HCl a) Tin chloride ($SnCl_2*2H_2O$, 0.2046 g) was dissolved in HCl (37%, 6.0 ml). Hexachloroplatinum ($H_2PtCl_6*6H_2O$, 0.0677 g) was dissolved in distilled water (10 ml). The two solution were mixed, and distilled water added to a total volume of 40 ml. Mg—Al HTC (14.7 g) was prepared according to Example 2a, but without drying. The salt solution was added to the wet carrier material in a dropwise manner (10 min). The final suspension was stirred for 1 hour, filtered, washed and dried overnight (100° C.). Part of the product was then calcined (560° C.) and tested under PDH conditions.

b) Part of the dried product was calcined at 800° C. and tested under PDH conditions.

EXAMPLE 16

Catalyst Testing of the Carrier Material

A carrier material prepared according to Example 1b was subject to a catalytic test under PDH conditions. GC analysis of the effluent gas showed negligible propane conversion (<1%) under the test conditions described above (>>General>>), but with shorter residence time (GHSV= 2400 $h^{-1}$).

EXAMPLE 17

Catalyst Testing

The catalysts prepared according to Examples 3–15 and 20 were subject to catalytic testing under PDH conditions. Test results obtained during the first 10 test cycles are shown in Table 2.

EXAMPLE 18

Catalyst Testing with Other Feedstocks a) Ethane dehydrogenation. A catalyst prepared according to Example 8 was used as an ethane dehydrogenation catalyst (See <<General>> for test conditions). The results obtained during six subsequent test cycles at 650° C. showed a stable activity from cycle to cycle, with an initial conversion of 40%, decreasing to 30% at the end of each test cycle. The selectivity towards ethene was 80–85%, on mole carbon basis. Before testing as an ethane dehydrogenation catalyst, the catalyst had been subject to PDH testing at 600° C.

b) Isobutane dehydrogenation. A catalyst prepared according to Example 8 was used as an isobutane dehydrogenation catalyst (See <<General>> for test conditions). The results obtained during three subsequent test cycles at 590° C. showed a rather stable activity from cycle to cycle, with an initial conversion of 58% (Cycle 1), 57% (Cycle 2) and 56% (Cycle 3), decreasing to 44% at the end of each test cycle. The selectivity towards butenes was 96%, on mole carbon basis. Before testing as an isobutane dehydrogenation catalyst, the catalyst had been subject to PDH testing at 600° C.

c) Propene hydrogenation. A catalyst prepared according to Example 12 was used as a propene hydrogenation catalyst (See "General" for test conditions). The catalyst had a high initial activity (74% conversion), decreasing to 32% during the first test cycle. The propane selectivity was 98–99% throughout the test.

EXAMPLE 19

Catalyst Calcination

A catalyst prepared according to Example 8 was subject to calcination at various temperatures (560–800° C.). Relative Pt dispersion values of the calcined samples were determined by CO pulse chemisorption experiments using an Alta-Mira apparatus (AMI-1) and the ROR pretreatment procedure. The results of the CO pulse chemisorption experiments are shown in Table 3. XRD showed a major MgO phase for all samples, and the BET area was in the range 150–200 $m^2/g$ for all samples (Table 1). PDH testing gave very similar results for the samples calcined at 560, 700 and 800° C. (Table 2). It should be noted that these results are not directly comparable with the other results in Table 2, due to a slightly modified pretreatment procedure.

EXAMPLE 20

Addition of Binder

A catalyst was prepared according to Example 8, and subsequently mixed with a lumina, before pressing, crushing, sieving and testing as a PDH catalyst. The results shown in Table 2 correspond to an alumina content of appx. 20 wt %. Similar test results were obtained with other alumina contents.

TABLE 1

Characterisation results for the materials described in the Examples.

| Material | Treatment | BET surface area ($m^2/g$) | XRD |
|---|---|---|---|
| Ex. 2a | Before calc. | 43 | HTC |
| Ex. 2b | After calc. | 145 | MgO |
| Ex. 3a | Before calc. | n.m. | MgO |
| Ex. 3a | After calc. | 202 | MgO |
| Ex. 3b | After calc. | 123 | MgO |
| Ex. 4 | After calc. | 129 | |
| Ex. 5 | After calc. | 162 | MgO |
| Ex. 6 | After calc. | 112 | MgO |
| Ex. 7 | After calc. | 113–126 | MgO |
| Ex. 8 | After calc. | 153 | MgO |
| Ex. 9 | After calc. | 106 | |
| Ex. 10 | After calc. | | MgO |
| Ex. 11 | After calc. | 111 | MgO |
| Ex. 12a | After calc. | | |
| Ex. 13 | After calc. | 156 | MgO |
| Ex. 14 | Before imp. | 135 | MgO (spinel) |
| Ex. 14 | After imp. and calc. | 110 | MgO (spinel) |
| Ex. 15a | After calc. | 172 | MgO |
| Ex. 15b | After calc. | 121 | MgO |
| Ex. 19 | Calcined 560/2 | 180 | MgO |
| Ex. 19 | Calcined 700/15 | 184 | MgO |
| Ex. 19 | Calcined 800/15 | 160 | MgO |

Abbreviations:
n.m.) Not measured

TABLE 2

Test results obtained with catalysts described in the Examples.

| | Cycle 1 conversion | | Cycle 3 conversion | | Cycle 5 conversion | | Cycle 10 conversion | |
|---|---|---|---|---|---|---|---|---|
| Catalyst | Initial | Final | Initial | Final | Initial | Final | Initial | Final |
| Ex.3a | n.m. | n.m. | 62 | 38 | 54 | 33 | n.m. | n.m. |
| Ex.3a | 53 | 35 | 46 | 30 | n.m. | n.m. | n.m. | n.m. |
| Ex.3b | 18 | 22 | $33^{II}$ $31^{III}$ | $24^{II}$ $22^{III}$ | n.m. | n.m. | n.m. | n.m. |
| Ex.4 | 68 | 47 | 59 | 43 | 46 | 32 | n.m. | n.m. |
| Ex.5 | 59 | 48 | 57 | 45 | $55^{I}$ | $38^{I}$ | 55 | 39 |
| Ex.6 | 55 | 43 | 61 | 44 | 60 | 40 | 60 | 36 |
| Ex.7 | 51 | 42 | 60 | 42 | 59 | 41 | 59 | 39 |
| Ex.8a | 50 | 33 | 60 | 45 | 60 | 44 | 60 | 41 |
| Ex.8b | 58 | 46 | n.m. | n.m. | 51 | 47 | n.m. | n.m. |
| Ex.9 | 54 | 48 | 55 | 41 | 54 | 48 | n.m. | n.m. |
| Ex.10 | 38 | 24 | 35 | 23 | 35 | 23 | n.m. | n.m. |
| Ex.11 | 52 | 47 | 52 | 40 | 51 | 38 | n.m. | n.m. |
| Ex.12a | 47 | 38 | n.m. | 50 | 58 | 47 | 55 | 40 |
| Ex. 12b | 57 | 45 | 55 | 42 | 55 | 41 | 52 | 38 ($9^{th}$) |
| Ex. 13 | 52 | 48 | 53 | 45 | n.m. | n.m. | 49 | 40 |
| Ex.14 | 59 | 40 | 55 | 31 | 58 | 28 | n.m. | n.m. |
| Ex.15a | 54 | 42 | 49 | 36 | 45 | 32 | n.m. | n.m. |
| Ex. 15b | 57 | 46 | 55 | 45 | n.m. | n.m. | n.m. | n.m. |
| Ex. 19/560° C. | 66 | 38 | 67 | 40 | 66 | 43 | n.m. | n.m. |
| Ex. 19/700° C. | 65 | 36 | 66 | 37 | 65 | 39 | 65 | 42 |
| Ex. 19/800° C. | 59 | 35 | 61 | 41 | 65 | 41 | 63 | 44 |
| Ex.20 | 55 | 23 | 57 | 29 | 56 | 30 | n.m. | n.m. |

Abbreviations:
n.m.) Not measured

[I]) Test cycle 6 (due to analytical problems)
[II]) Test cycle 2
[III]) Test cycle 3

TABLE 3

Influence of calcination temperature on metal dispersion (Example 19)

| Calcination temperature (duration) (° C.) (hours) | Relative metal dispersion |
|---|---|
| 560 (2) | 1.0 |
| 560 (15) | 1.0 |
| 700 | 1.4 |
| 800 | 1.6 |

DISCUSSION

The characterisation results shown in FIGS. 1–3 and in Table 1 illustrate that when contacting a calcined hydrotalcite-based material with an aqueous solution, the hydrotalcite phase is regained. After subsequent calcination, the hydrotalcite phase transforms to the oxide phase.

However, when contacting a calcined hydrotalcite-based material with an ethanol solution, the oxide structure is maintained.

It has previously (See: <<General>>) been stated that the selectivity of the catalysts prepared according to the present invention, is very high. The major focus of this discussion is therefore on the activity and stability of dehydrogenation catalysts prepared according to the present invention. From the results in Table 2, it is observed that the initial conversion level of the catalysts is generally high during propane dehydrogenation (appx. 60%), and very close to the thermodynamic equilibrium conversion under these conditions. When discussing the catalyst stability, focus is therefore put on the activity at the end of each test cycle, denoted < conversion>> in Table 2. When reporting that the catalyst reaches a stable performance level, this means that it's final conversion is similar for several consecutive test cycles. In general, the test results (Table 2) illustrate that the catalysts prepared according to the present invention (i.e.; metal addition, washing and calcination) reach a stable performance level between the $5^{th}$ and $10^{th}$ test cycle.

The test results shown in Table 2 further illustrate that catalysts prepared according to our previous invention[1] (i.e.; oxide phase of carrier material during metal addition, Example 3), have a life time stability and/or a stable performance level which is clearly inferior to that obtained for samples prepared according to the present invention (i.e.; hydrotalcite phase during metal addition, preferably followed by washing, e.g. Examples 5–9). This means that it is important to add the metal(s) to the hydrotalcite phase, and then calcine it at the desired temperature. Table 2 further illustrates the strong influence of the washing step on the stable performance level of each catalyst (Example 4 vs. Example 5; and Example 8 vs. Example 10). The same trends are observed regardless of the Mg/Al ratio of the hydrotalcite-based carrier material.

The metal addition procedure (dry or wet carrier, dropwise or >>one go>> metal addition, carrier metal solution contact time) has only a minor influence on the catalyst's initial activity and life time stability.

The characterisation results shown in Table 1 and 3 illustrate that the final calcination temperature may be varied compared to the standard calcination temperature (560° C.), while maintaining a high metal dispersion and high specific surface area. The corresponding test results (Table 2) illustrate that the calcination of the final catalysts at temperatures above 560° C. leads to catalysts with maintained or improved long-term stability.

The results in Table 2 further indicate that the impregnation of an uncalcined hydrotalcite, which is subsequently calcined at 560° C., gives a catalyst with a lower deactivation rate within each test cycle, but with a lesser long-term stability compared to catalysts based on pre-calcined carrier materials.

Replacing Al in the hydrotalcite phase with Ga does not lead to an improved catalyst compared to carrier materials containing only Mg and Al.

Addition of an alumina binder leads to a more rapid deactivation during each test cycle, but does not alter the long-time stability of the catalyst.

The use of a modified pretreatment procedure (Ex. 8b (and Ex. 19) compared to Ex. 8a) gave a higher conversion in the first test cycle, but did not alter the long-term stability of the catalyst.

The dehydrogenation tests using other feedstocks than propane (Example 18) illustrate that the excellent activity and stability properties observed for the catalysts of the present invention, are properties which are of general validity to all types of hydrocarbon dehydrogenation reactions. It is further observed that the catalysts of the present invention are also excellent catalysts for the hydrogenation of unsaturated compounds (Example 18). The particular benefits thus obtained by using the catalysts of the present invention were not to be expected in view of the prior art comprising the references as listed below.

REFERENCES

1. Akporiaye, D.; Rønnekleiv, M.; Hasselgård, P.; to Statoil; PCT/NO94/00102 (1994), (22 pp).
2. Rytter, E.; Akporiaye, D.; Olsbye, U.; to Statoil; Norwegian Patent Application No. 1998.1126, (1998).
3. Cavani, F.; Trifiró, F.; Vaccari, A.; Cat. Today, 11(2), (1991), 171–301.
4. Miyata, S.; Iijima, N.; Manabe, T.; to Kyowa Chemical Industry Co.; EP 0 152 010 B1, (1985), (10 pp).
5. Sato, T.; Wakabayashi, T.; Shimada, M.; Ind. Eng. Chem. Prod. res.; 25, (1986), 89–92.
6. Clause, O., Gazzano, M, Trifiro, F., Vaccari, A and Zatorski, L., Appl. Cat., 73, (1991), 217.
7. Davis, R. J, and Derouane, E. G.; Nature, 349, (1991), 313–315.
8. Drezdzon, M. A.; Moore, E. J.; Kaminsky, M. P.; to Amoco Corp.; U.S. Pat. No. 4,843,168, (1989), (8 pp).
9. Fukuhara, H.; Matsunaga, F.; Nakashima, Y.; to Mitsui Petrochemical Industries Ltd.; EP 0 323 192 B1; (1988), (7 pp).
10. Matsunaga, F.; Fukuhara, H.; to Mitsui Petrochemical Industries Ltd.; EPA 0 332 380 A2; (1989), (4 pp).
11. Delzer, G. A.; Kolts, J. H.; to Phillips Petroleum Company; EPA 0 330 224 A1, (1989), (6 pp).
12. Derouane, E.; Davis, R. J.; Blom, N. J.; to Haldor-Topsoe; EP 0 476 489 B1, (1991), (13 pp).
13. Davis, R. J.; Mielczarski, E.; in: <<Selectivity in Catalysis>>; Am. Chem. Soc.; (1993), 327–336.
14. CRC Handbook of Chemistry and Physics, $62^{nd}$ Ed.; CRC Press, Florida, (1981–82).
15. Khare, G. D.; Porter, R. A.; to Phillips Petroleum Company; U.S. Pat. No. 5,430,220, (1994); (6 pp)
16. Barias, O. A.: <<(Transient kinetic investigation of catalytic dehydrogenation of propane>>, Ph, D. Thesis, NTH, Inst. For Industrial Chemistry, Trondheim, (1993).
17. Misra, C.: U.S. Pat. No. 4,656,156 (1987), 9 pp.

What is claimed is:

1. A process for preparing a catalyst comprising at least one catalytic metal loaded on a hydrotalcite-based carrier material which has the following formula in its uncalcined form $$M^{2+}_a M^{3+}_b (A^{n-})_c (OH)_{2a+3b-nc} * xH_2O,$$

wherein $M^{2+}$ is at least one divalent metal; and $M^{3+}$ is at least one trivalent metal;
A is an n-valent anion
n is 1 or 2,
c is 1 or 2,
and a and b are positive numbers, a>b; which process comprises:
a) adding at least one catalytic metal salt or complex to the carrier material, of which the carrier material is in, or at least partly transformed to, the hydrotalcite phase during the metal addition step;
b) followed by washing, and
c) calcination.

2. The process of claim 1, wherein the catalytic metal is at least one metal selected from Group VIII of the periodic table of elements.

* * * * *